(12) United States Patent
Lysen

(10) Patent No.: US 6,553,837 B1
(45) Date of Patent: Apr. 29, 2003

(54) PROCESS AND APPARATUS DEVICE FOR ANALYSIS OF ROLLER BEARINGS IN MACHINES

(75) Inventor: Heinrich Lysen, Garching (DE)

(73) Assignee: Pruftechnik Dieter Busch AG, Ismaning (DE)

( * ) Notice: Subject to any disclaimer, the term of this patent is extended or adjusted under 35 U.S.C. 154(b) by 0 days.

(21) Appl. No.: 09/637,582

(22) Filed: Aug. 14, 2000

(30) Foreign Application Priority Data

Aug. 16, 1999 (DE) .......................................... 199 38 722

(51) Int. Cl.⁷ ................................................. G01H 1/00
(52) U.S. Cl. ............................ 73/579; 73/598; 73/602; 73/659; 73/660
(58) Field of Search .................... 73/579, 597, 598, 73/599, 600, 602, 593, 659, 660, 663; 702/39, 56

(56) References Cited

U.S. PATENT DOCUMENTS

| | | | |
|---|---|---|---|
| 3,554,012 A | | 1/1971 | Söhoel ........................ 73/579 |
| 4,007,630 A | | 2/1977 | Noda .......................... 73/593 |
| 4,456,313 A | | 6/1984 | Hartnett et al. ............. 384/565 |
| 4,763,523 A | * | 8/1988 | Womble et al. ................ 73/587 |
| 4,884,449 A | * | 12/1989 | Nishimoto et al. ............ 73/660 |
| 5,005,417 A | * | 4/1991 | Kawasaki et al. ............. 73/593 |
| 5,072,611 A | * | 12/1991 | Budd et al. ................. 73/118.1 |
| 5,150,618 A | * | 9/1992 | Bambara ..................... 73/660 |
| 5,511,422 A | * | 4/1996 | Hemandez .................... 73/593 |
| 5,663,894 A | * | 9/1997 | Seth et al. .................... 73/579 |
| 5,852,793 A | * | 12/1998 | Board et al. ................... 702/56 |
| 5,895,857 A | * | 4/1999 | Robinson et al. ............. 73/660 |

FOREIGN PATENT DOCUMENTS

| | | |
|---|---|---|
| DE | 29 47 937 A1 | 11/1981 |
| DE | 41 27 395 | 2/1993 |
| EP | 0 800 072 A2 | 10/1997 |
| WO | WO 96/30825 | 10/1996 |
| WO | WO 98/09140 | 3/1998 |

OTHER PUBLICATIONS

Ingobert Schmid et al., Minimization of Torsional Vibrations from Cynamic Transmission Test Stands, in ATZ–Automobiltechnische Zeitschift 85 (1983), 1, pp. 25–30.

Martin Molitor, Fehlerfreiheit Als Ziel, in QZ 37 (1992), 12, pp. 735–739.

Wolfgang Scheithe et al., Schwingungsmessung zur Früherkennung Von Wälzlagerschäden, in: VFI 1/90, pp. 56–60.

Wolfgang Scheithe et al., Schwingungsmessung zur Früherkennung von Wälzlagerschäden, in: VFI 2/90, pp. 60–63.

Daniel J. Inman, Vibration with Control, Measurement, and Stability, Prentice Hall, Englewood Cliffs, New Jersey, 1989, pp. 2, 12, 13, and 294.

Klein, "Vibration–diagnostic Assessment of Machines and Systems", pp. 69–89, 6.1 Wälzlager.

* cited by examiner

*Primary Examiner*—Hezron Williams
*Assistant Examiner*—Jacques M. Saint Surin
(74) *Attorney, Agent, or Firm*—Nixon Peabody LLP; David S. Safran

(57) ABSTRACT

The invention relates to a process for analysis of roller bearings (15) which have been installed in machines, by means of a sensor (10) a signal being recorded which is produced by the rolling motion, and the signal amplitude is evaluated in order to determine the presence and optionally the depth of the damage in the roller bearing running surface (56). In doing so a dynamic model of the roller bearing in the machine is considered, in which at least the bilateral contact stiffnesses (4, 6) of the rolling elements are considered in order to determine the transfer function between the force caused by the damage and the corresponding sensor signal which is then taken into account in the signal amplitude evaluation. The invention furthermore relates to a corresponding analysis device.

33 Claims, 4 Drawing Sheets

PROCESS AND APPARATUS DEVICE FOR ANALYSIS OF ROLLER BEARINGS IN MACHINES

This invention relates to a process and device for analysis of roller bearings installed in machines, a sensor recording the signal which is produced by the motion of the rolling element and the signal amplitude being evaluated in order to determine the presence and optionally the depth of damage in the roller bearing running surface.

Damage on the running surface of roller bearing rings in bearing operation each time a rolling element rolls over the damage site leads to excitation of vibration of the roller bearing and the machine components which are mechanically coupled to it. Here, conventionally by means of an acceleration transducer which is coupled for example to a bearing block, an acceleration signal is determined which results from the deflection or the absorption of force of the rolling element at the damage site. For diagnosis of the roller bearing state especially the depth of existing damage is of interest.

A survey of vibration-diagnostic methods for roller bearings is known from section 6.1 of *Vibration-diagnostic Assessment of Machines and Systems* by Ulrich Klein, published by the Association for Operating Strength Research, Steel-Iron Publishing House, Duesseldorf, 1998. It describes for example transducer resonance techniques, the sensor signal being subjected to bandpass filtration around the resonant frequency of the sensor. In impact-pulse measurement the average value of the sensor signal is found, while in the SEE method the time derivative of the acceleration is formed and its intensity in the range of high frequencies up to 300 kHz is analyzed. In the spike energy method the bandpass-limited acceleration average, the envelope curve of the alternating amplitudes and the peak value relative to the effective value are analyzed, the results being evaluated by means of empirically determined normalization to the rpm and the bearing diameter. The defect in this method is that damage on the inner ring can hardly be detected and furthermore for certain types of machines, normalization is not appropriate. Furthermore, the indicated book describes processes in which the peak holding capacity of the amplitude distribution and the statistical distribution are evaluated.

Furthermore, for normalization of the acceleration signal amplitude after envelope curve formation in the time domain, the attempt was made to draw conclusions regarding the transfer function of damage excitation from the structure resonances or the tone frequencies of the bearing components. This process however did not deliver satisfactory results since the structure resonances or tone frequencies of the bearing components in the unclamped state hardly allow conclusions regarding the transfer behavior of the installed bearing.

Other examples for evaluation of the envelope curve signal in the time domain can be found in U.S. Pat. No. 4,007,630 and U.S. Pat. No. 3,554,012.

The object of this invention is to devise a process and device for analysis of roller bearings in machines, by means of which conclusions regarding the depth of damage in a roller bearing running surface are reliably possible from the signal amplitude.

This object is achieved as claimed in the invention by a process as claimed in claim 1 and a device as claimed in claim 32.

In the approach as claimed in the invention it is advantageous that realistic normalization of the signal amplitude is enabled by at least approximate determination of the transfer function so that reliable evaluation of the damage depth is enabled.

Preferred embodiments of the invention follow from the dependent claims.

One embodiment of the invention is detailed by way of example using the attached drawings.

FIG. 1 schematically shows a side view of a machine with two radial roller bearings;

FIG. 2 shows a front view of the machine from FIG. 1;

FIG. 3 schematically shows a vibration model of the machine from FIGS. 1 and 2;

Figure 7:
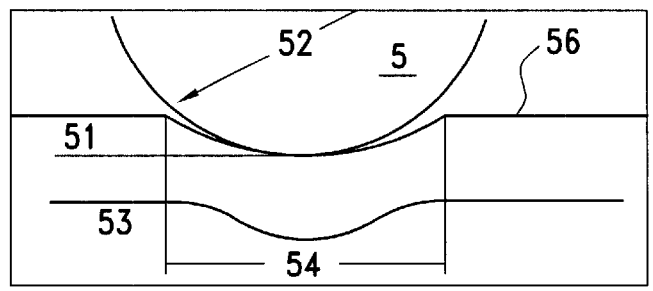
Figure 8:
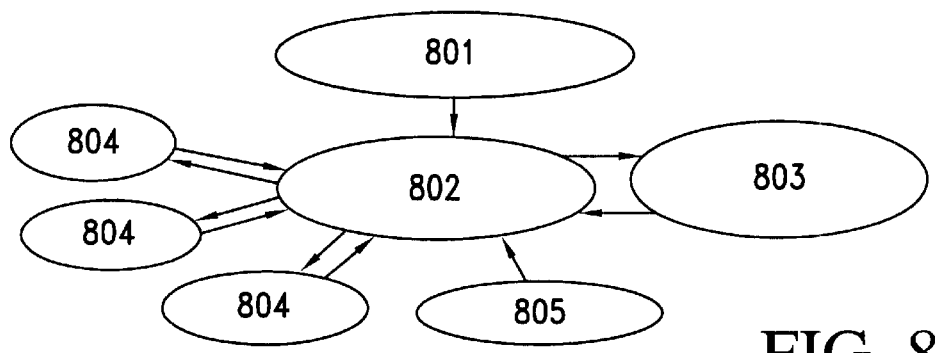
Figure 9:
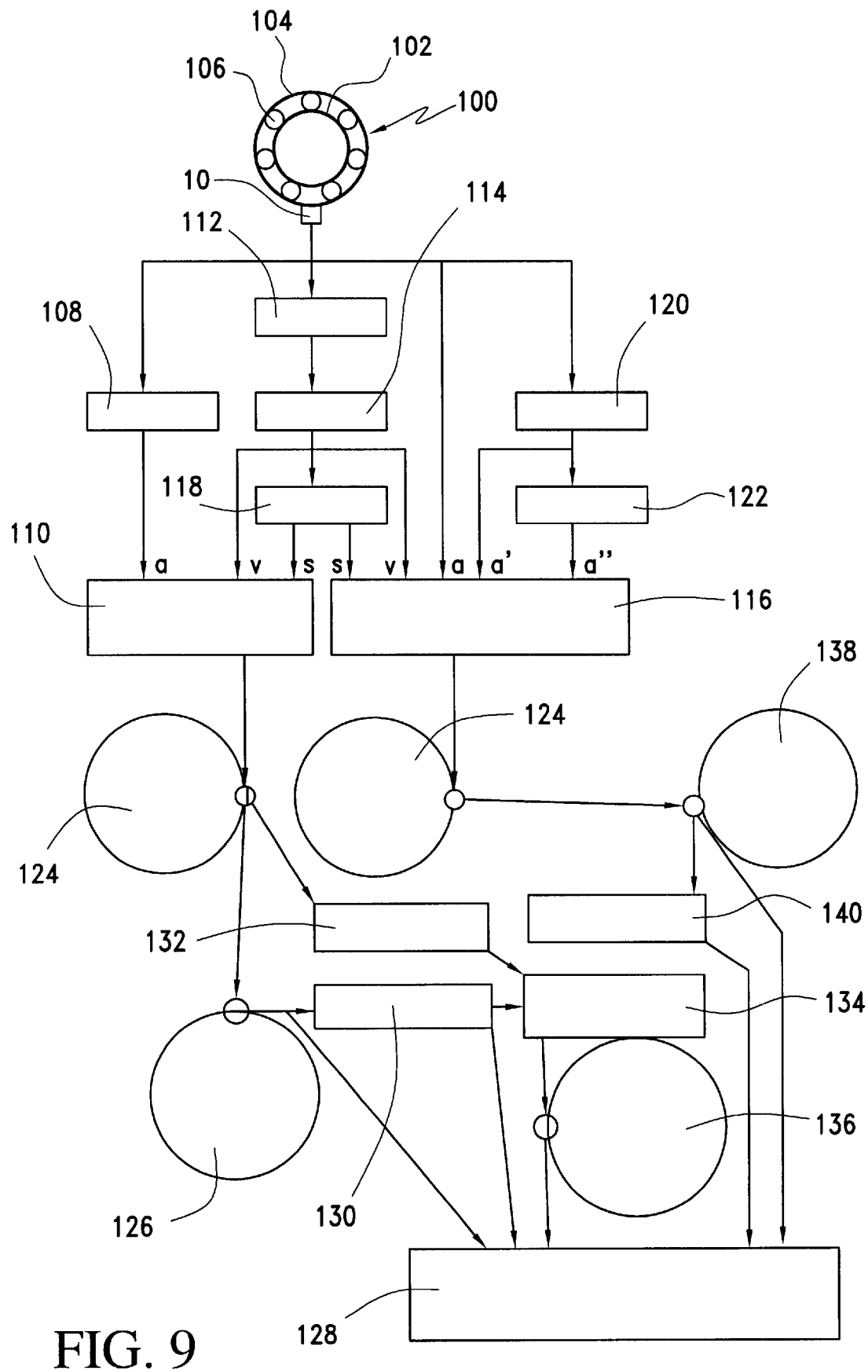
Figure 10:
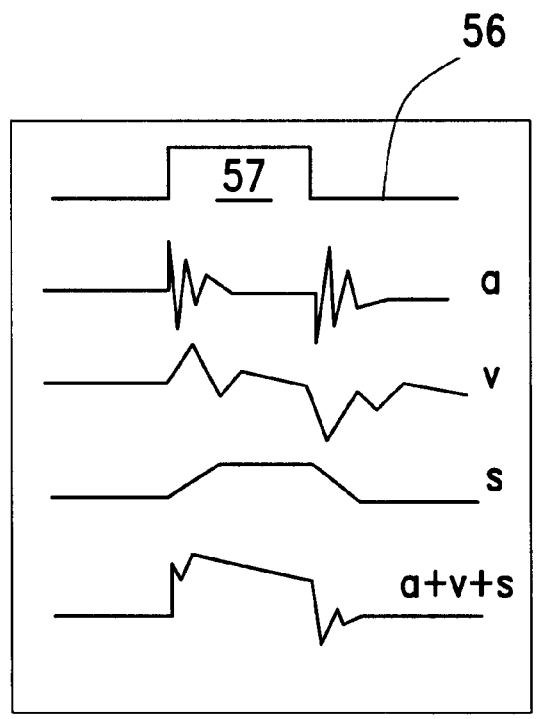
Figure 11:
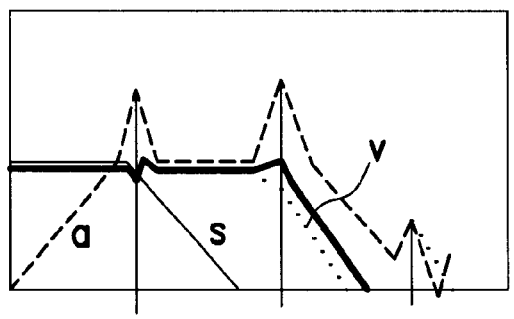

FIG. 7 schematically shows damage to a running surface which is rolled over by a rolling element;

FIG. 8 shows by way of example the information flow in the rolling element analysis device as claimed in the invention;

FIG. 9 schematically shows the structure of a roller bearing analysis device as claimed in the invention;

FIG. 10 shows the sample characteristic of a damage profile and the corresponding path, speed and acceleration signals and the sum thereof; and FIG. 11 shows the frequency responses of the path, speed and acceleration signal and the sum thereof.

Figure 1:
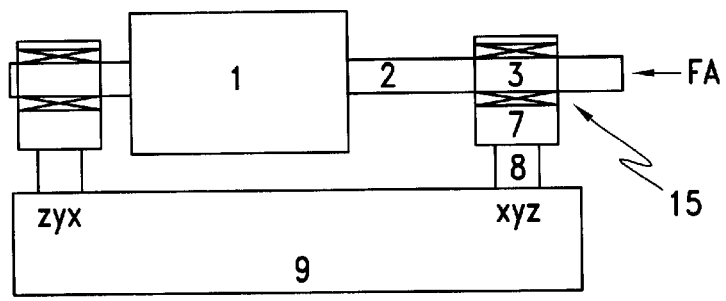
Figure 2:
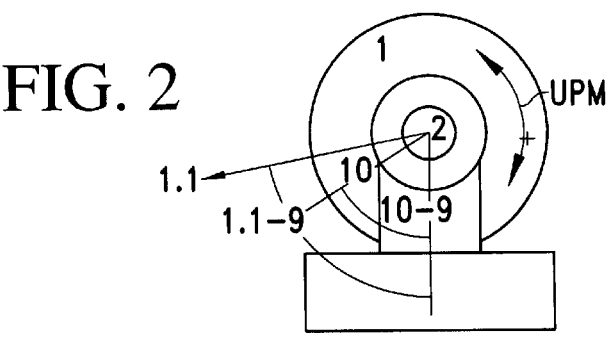

The machine shown in FIGS. 1 and 2 comprises a rotor with a mass 1, a shaft with stiffness 2 and mass 3 which is connected to the inner ring (not shown) of the roller bearing 15, a bearing block with mass 7 and stiffness 8, which is connected to the outer ring (not shown) of the roller bearing 15, and a machine foundation with a mass 9, an acceleration transducer 10 being connected to the bearing block 7. The roller bearing 15 which is made as the radial bearing comprises several rolling elements which have contact stiffness 4 with respect to their contact with the inner ring, contact stiffness 6 with respect to their contact with the outer ring, and a mass 5. FIG. 1 shows the direction of rotation of the rotor 1 with RPM, the force additional to gravity or the balanced load (for example, an unbalance force) is labeled I.1, the angle between the direction of the transducer 10 and the direction of gravity is labelled 10-9 and the angle between the additional force and gravity is labeled 1.1-9.

Figure 3:
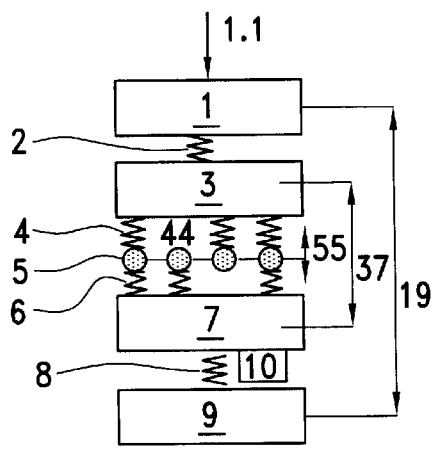

FIG. 3 shows a vibration model for the machine from FIGS. 1 and 2, the rotor mass 1 being coupled via the shaft stiffness 2 to the shaft mass 3, to which the rolling element masses 5 are coupled via the contact stiffness 4 of the rolling element (i.e. the rolling element masses 5 are coupled via the contact stiffness 4 to the inner ring). Furthermore, the rolling element masses 5 are coupled via the rolling element contact stiffness 6 to the bearing block mass 7 (i.e. the rolling element masses 5 are coupled to the outer ring via the contact stiffness 6), the bearing block mass 7 to which the acceleration transducer 10 is coupled being coupled to the machine foundation mass 9 via the bearing block stiffness 8. In addition to the gravitational force of the masses 1, 3, 5, 7 and 9, the additional load 1.1 (for example, an unbalance) acts on the rotor mass 1 in the system. The system from FIG. 3 has three major resonant frequencies, specifically the resonance or resonant frequency of the rolling element 5 which is labelled 55, the resonance or resonant frequency between the shaft mass 3 and the bearing block mass 7 which is labeled 37 (hereinafter called the bearing resonance) and the resonance or resonant frequency between the rotor mass 1 and the foundation mass 9 which is labeled 19. The structure resonances or tone resonances of the individual machine components or bearing components, i.e. the resonances in the uncoupled or free state, play no part in the vibration model of FIG. 3 used for evaluation of the signal of the transducer 10.

With respect to the contact stiffnesses 4 and 6 of the rolling elements, the following particulars must be considered: The contact stiffnesses 4 and 6 of the rolling elements are to a certain extent dependent on force, the force depending on the number of instantaneously supporting rolling elements. The number of supporting rolling elements in turn depends on the bearing clearance, i.e. the radial play between the inner ring and the outer ring, and the total force on the bearing. The total force on the bearing, which essentially comprises gravity, the unbalance force, the axial force (in FIG. 1 labelled Fa) and the centrifugal force, is dependent on rpm and on time due to the centrifugal force and the unbalance force, the centrifugal force acting only on the contact stiffness 6 of the outer ring of the rolling element. The distribution of the total force is dependent on the diameters of the rolling elements and their shape.

Inner ring contact damage and outer ring contact damage are labelled 44 and 66 in FIG. 3, it being assumed in the following that it is damage in the running surface of the inner ring and the running surface of the outer ring. Likewise contact damage could of course also be formed by damage on the running surface of a rolling element, the damage however then occurring according to the rolling element rolling alternately in inner ring contact and outer ring contact. For the sake of simplicity these cases will not be examined here. FIG. 7 schematically shows damage to the running surface of the inner ring and the outer ring as a depression in the running surface into which a rolling element 5 with a diameter 52 plunges. The damage depth 51 is the path by which the rolling element 5 when rolling over the damage in the radial direction "plunges" or is deflected with respect to the undamaged running surface 56. In the following, 100% effective damage depth will be considered the damage depth at which a rolling element 5 can plunge so deeply into the damage that it no longer bears the sum of the forces which are instantaneously acting on it, i.e. at 100% effective damage depth the running surface at the damage site no longer contributes to the bearing action and is in this sense 100% damaged. The reference to the instantaneously acting forces makes sense in that for underloaded bearings otherwise a damage depth of 100% would never be determined and the bearings could still fail (a damage depth of more than 100% is possible when several rolling elements are no longer supporting at the same time, for example, in stationary erosion). The contact faults 44 and 66 in FIG. 3 in this sense can be defined as 100% effective, i.e. the running surface is no longer supporting at this site.

FIG. 10 schematically shows which path signal s, velocity signal v and acceleration signal a are produced by damage 57 in a running surface 56 when rolled over by a rolling element 5, a depression with steep edges which is relatively long with respect to the diameter 52 of the rolling element being assumed. When plunging or emerging from the damage 57 the rolling element 5 in the acceleration signal a produces a pulse-like excitation, while in the velocity signal v, more uniform, wider excitation occurs. Conversely, flat, wide excitation which essentially corresponds to lowpass filtration of the damage profile appears in the path signal. Accordingly, the acceleration signal a is suited mainly for damages which are short relative to the diameter 52 of the rolling element, while the velocity signal v is suitable for medium and the path signal s for long damages.

Figure 4:
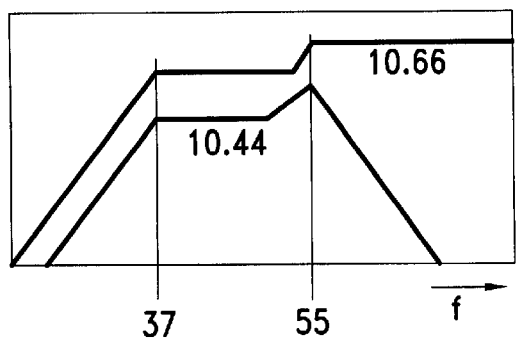
FIG. 4 shows by way of example the frequency-dependent transfer function for inner ring damage or outer ring damage.
Figure 5:
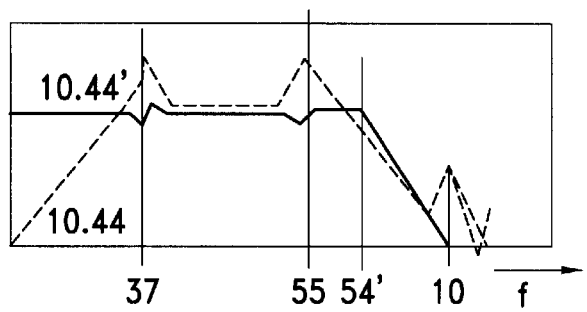
FIG. 5 shows a sample frequency-dependent transfer function for inner ring damage (broken line) and a transfer function which has been linearized as claimed in the invention (solid line)
Figure 6:
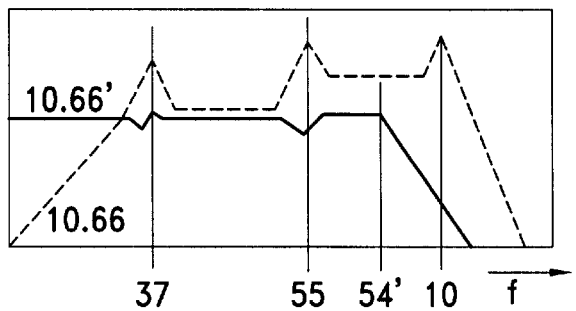
FIG. 6 shows the same thing as FIG. 5, but for outer ring damage.

FIG. 4 shows the frequency-dependent transfer functions for an inner ring contact fault 44 or outer ring contact fault 66, i.e. the frequency-dependent ratio between a force change 44 and 66 produced by the damage and the corresponding acceleration at the coupling site of the vibration transducer 10, as follows from the vibration model from FIG. 3. This shows that the transfer behavior for inner ring damage (labelled 10.44 in FIG. 4) differs from that of outer ring damage (labelled 10.66 in FIG. 4) mainly in the area on the other side of the resonant frequency 55 of the rolling element, where excitation caused by inner ring damage is damped with increasing frequency, while excitation caused by outer ring damage is not damped. It is common to both types of damage and damage sites that in the region between the bearing resonance 37 and the rolling element resonance 55 the transfer function is flat, i.e. the acceleration at the coupling site of the acceleration sensor 10 is roughly proportional to the force change 44 and 66 produced by the damage, while in the region underneath the bearing resonance 37 the propagation of the two excitations is damped with decreasing frequency. Without correcting the frequency response or transfer function for the outer ring damage and inner ring damage, thus only in the area between the bearing resonance 37 and the rolling element resonance 55, from the acceleration amplitude as is determined with the transducer 10 could conclusions be drawn regarding the damage depth (which is linked to the change of force at the damage site via the contact stiffness) since only in this area is there the required proportionality between the excitation caused by the damage (change of force 44 and 66, i.e. damage depth) and the acceleration signal. But since in general relevant damage signals also occur outside this frequency range, for reliable scaling or evaluation of the amplitude of the damage signal it is necessary to linearize the frequency response or damage transfer function in the entire frequency range in which damage signals can occur, as is shown in FIGS. 5 and 6 with the solid line. FIGS. 5 and 6 additionally show by means of the broken line the corresponding uncorrected frequency response for inner ring contact damage or outer ring contact damage, in addition to FIG. 4 the resonance of the transducer 10 being considered (in FIGS. 5 and 6 the corresponding resonant frequency is labelled with reference number 10).

Reference number 54' in FIGS. 5 and 6 labels a frequency which is hereinafter called the "highest energy maximum damage frequency", this being calculated as follows. The circle segment penetrating the damage (or flattened circle segment) can be computed from the 100% effective damage depth (labelled 51 in FIG. 7) and the diameter 52 of the rolling element. This yields the scanning shape which is labeled 53 in FIG. 7 and which corresponds to the profile 55 of the running surface as seen from the rolling element 5 rolling over the damage, and thus corresponds to the force in the rolling element 5. In FIG. 7 the length of the penetrating circle segment is labelled 54, the inverse of the length 54 corresponding to the local frequency of the shortest possible 100% effective damage which can be converted into a (time) frequency by the rollover velocity of the rolling element 5. The frequency obtained in this way corresponds to the highest energy maximum damage frequency 54'. It goes without saying that the scanning shape or damage shape 53 also contains even higher frequency portions and thus produces acceleration damage signals with higher frequencies, however a lower energy accruing to these higher frequency portions than to frequency 54'. For this reason it is sufficient for reliable signal amplitude evaluation if the transfer function 10.44' and 10.66' is linearized at least up to this highest energy maximum damage frequency, as is shown in FIGS. 5 and 6.

In the frequency range in which the transfer function is linear, i.e. in the representation of FIGS. 5 and 6, flat, since then the change 44 and 66 of the force at the damage site when a rolling element 5 rolls over it is proportional to the acceleration measured by means of sensor 10, the damage depth 51 can be computed from the measured acceleration amplitude and the contact stiffness 4 and 6 of the rolling element, and since the sensor 10 records the acceleration on the bearing block mass 7, normalization thereto being necessary. The damage depth is thus formed as the product of the acceleration signal amplitude times the bearing block mass divided by the contact stiffness of the rolling element. For an uncorrected frequency response 10.44 and 10.66 it applies as mentioned above only to the frequency range between the bearing resonance 37 and the resonance 55 of the rolling element. The resonant frequencies 37 and 55 in turn can be computed by means of the vibration model when the parameters which enter into the vibration model of FIG. 3 are known. Outside this area on the other hand linearization of the transfer function is necessary to be able to draw conclusions about the damage depth from the acceleration signal amplitude. For a complete description of the machine from FIGS. 1 and 2 by means of the vibration model from FIG. 3 it is necessary to know the force of gravity, the unbalance force, optionally the axial force Fa, the centrifugal force of the rolling elements, the stiffnesses 4, 6, 2 and 8 of the rolling elements, the shaft and the bearing block and the masses 7, 1, 5 and 9 of the bearing block, of the rotor, of the rolling elements and of the foundation. But here not all parameters are equally important for amplitude evaluation and they can be estimated or omitted. The parameter which is most important for the amplitude evaluation is however the contact stiffness 4 and 6 of the rolling elements so that this is taken into account in any case, but for example when the signal is evaluated with respect to the inner ring damage amplitude optionally only the inner ring contact stiffness 4 being considered and in an analysis with respect to outer ring damage only the outer ring contact stiffness 6 being considered.

Preferably however all these parameters are considered in order to obtain a vibration model of the machine as relevant as possible and thus to be able to correct the acceleration signal amplitude as reliably as possible with respect to the transfer function in order to be able to indicate the damage depth responsible for the acceleration signal as accurately as possible.

FIG. 8 schematically shows the data flow for a roller bearing analysis system, for a certain machine type, a certain design or a certain series the relevant characteristics or parameters being formed as a function of the bearing diameter (this is indicated at 803) and stored in a database 802. If a machine is to be analyzed which has not yet been typified in this way, the required characteristics can be acquired with computer support on site (this is indicated in 804), the acquired data flowing into the database and if several machines of this type have already been recorded, can be typified according to 803. In FIG. 8 the data flow from the machine manufacturer or bearing manufacturer is labelled 801, while the data flow is labelled 805 when checked damage cases are reported back.

The database 802 contains for example bearing data of the following type: combined bearings are divided into individual bearing types and are evaluated in succession. For multi-series bearings, the series number is considered for the total stiffness and the number of supporting rolling elements. The bearing stiffness given by the bearing manufacturer is divided into inner ring contact stiffness and outer ring contact stiffness, the sum of the spring constants remaining constant and the shape of the rolling elements and running surface being considered by osculation, for example the following "osculating stiffnesses" can be considered: cylinder-surface: cs=32, ball-groove: cs=8, ball-surface cs=2. Furthermore, the number and the length or mass of the rolling elements, the diameter of the graduated circle, the diameter of the rolling element, the contact angle for the rollover frequencies and the bearing clearance are considered.

In the recording of a not yet typified machine on site according to 804 for example it is possible to proceed as follows: first the vibration model as shown in FIGS. 1, 2 and 3 is edited, from the input of the machine geometry the masses, forces and shaft stiffnesses following. The transfer ratios and the transfer function between the shaft and the bearing block or the bearing block and the foundation are measured, a second transducer, especially on the bearing foundation, can be provided to measure the transfer ratio when the machine is running, or by carrying out a striking test with the machine stationary, one machine element being excited in a pulse-like manner and the system response being acquired with the acceleration transducer. But fundamentally also the system formed from the bearing and machine could also be modelled by means of the finite element method. The vibration model is also suitable for treatment of distributed mass-spring vibration systems by this transmission of the transfer ratios between the shaft and the bearing block or the bearing block and the foundation.

Finally, estimated values for the resonant frequencies are determined from the bearing data. If bearing damage is found with these estimated values, the resonant frequencies which occur are measured and the estimated values are improved. Since, as already mentioned above, all vibration model parameters are not always relevant to the result and moreover are not always mathematically linked among one another, often some of the parameters can be omitted or only a rough estimate is necessary. The analysis system is made such that it indicates to the user which data are necessary and which can be used by way of replacement.

The values determined in this way are settled among one another and finally corrected with the angle of the transducer with reference to the resulting load direction (multiplication by $1-\cos\alpha$) so that the damage and the characteristics of the recorded machines are obtained.

Preferably the database 802 is made such that a "self-learning function" is implemented, the parameters making up the vibration model being checked by means of checking the results delivered by the model and being optionally corrected. Here the data stored in the database 802 are evaluated with a confidence factor which reflects the origin and thus the reliability of the respective parameter. Thus, for example remeasured data themselves can be rated 100%, manufacturer data 90%, indirectly measured data 80%, data determined from typifying (803) 70%, indirect manufacturer data computed from other information 60%, data computed from information of other manufacturers 50%, repeatedly indirectly measured data 40%, estimates 30%, data of unknown origin 20% and default data 10%. After each successful measurement, i.e. when damage has been found, all machine and bearing data (804) flow back into the database, a compensation computation taking place with consideration (weighting) of the confidence factors. But only data are corrected with a confidence factor less than 100% are corrected. Also the confidence factors are matched accordingly to the result of checking, in the correction of data the old and the new confidence factor being considered. The confidence factors can be matched for example by the confidence factor being set to (old confidence factor+ 100%)/2 for found damage.

In particular, for damage determined by the system the corresponding bearing can be dismounted and inspected to verify the damage. If in doing so the analysis result of the system is confirmed, a success report 805 is delivered and the corresponding data are corrected with the residual error, its confidence factor for example again can be increased to (old confidence factor+100%)/2. If the damage diagnosis of the system is not confirmed, the causes for this must be studied.

Overall the database can be continually improved by the described approach, by which the data become increasingly more reliable and the diagnosis accuracy can be improved.

The linearization of the damage transfer function shown in FIGS. 5 and 6 can however also be accomplished for example by forming from the determined transfer function the function which is inverse thereto in order to filter the measured acceleration signal in order to determined the "genuine" damage amplitude and thus the damage depth.

The linearization of the transfer function can however also be achieved by the velocity signal v and the path signal s being formed from the measured acceleration signal a by integration and the sum of these three signals being formed with a certain weighting (see FIG. 10). If in this case the weighting of the individual signals is chosen correctly, a reconstruction of the damage profile (compare FIG. 10 top and bottom) results. Correct weighting of signals can be determined from the vibration model, the frequency-dependent transfer functions for the velocity signal and the path signal being determined in a similar manner as for the acceleration signal and the velocity signal and the path signal being then weighted such that their transfer functions at the bearing resonance 37 have a value 1, i.e. amplification 1, see FIG. 11, where the transfer functions for the inner ring damage are shown. In this case, for the summation signal the frequency response is formed which is given in FIG. 11 with the thick solid line and which is flat at least up to the rolling element resonance 55, i.e. linear. In particular the addition of the acceleration signal a and the path signal s based on the phase shift of 180° between the two signals results in suppression of the bearing resonance 37, see FIG. 11.

FIG. 9 schematically shows a device for executing the just described process, on a roller bearing 100 with an inner ring 102, an outer ring 104 and several rolling elements 106 an acceleration signal being recorded which is caused by the motion of the rolling element 106 by means of an acceleration transducer 10 which is coupled to the outer ring 104. The output signal of the sensor 10 is divided among four branches, the first after passing through a lowpass 108 with the corner frequency which corresponds to the highest energy maximum damage frequency 54' being supplied to a summer 110. By means of the lowpass 108, disruptive high-frequency portions, especially the transducer resonance, are masked out. Another branch is supplied to an integrator 112, signal portions which have the periodicity of rotation of the supported shaft being removed from its output signal by a rotation period suppression stage 114. The velocity signal obtained in this manner is on the one hand sent to the summer 110 and on the other hand to a summer 116 and an integrator 118. The output signal of the integrator 118 which corresponds to the path signal s is supplied both to the summer 110 and also the summer 116. The third branch of the measured acceleration signal a is supplied to the summer 116, while the fourth branch is subjected to double differentiation by means of a differentiator 120 and a differentiator 122. The output signals of the differentiator 120 and 122 are supplied to the summer 116.

The amplifications of the integrators 112 and 118 are set such that weighting of the signals a, v, and s which is formed according to the aforementioned rule arises in the summer 110. The correct weighting for the first and second derivative of the acceleration in the sum formed in the summer 116 arises by the corresponding setting of the two differentiators 120 and 122, the frequency response of the first and the second derivative being determined and the weighting being chosen such that the two derivatives at the rolling element resonance 55 have the same amplification in order to compensate for the drop of the transfer function for the acceleration signal or the sum signal from a, v, and s on the other side of the rolling element resonance 55.

The output signal of the summer 110 is used to evaluate the signal with respect to outer contact damage or outer ring damage, while the output signal of the summer 116 is used for evaluation of the signal with respect to the inner contact damage or inner ring damage. Overall, the previously described signal conditioning is signal conditioning which is proportional to the damage length and in which by means of the transmission path from the damage site to the transducer 10 signal distortions which have taken place by the nonlinear transfer functions are compensated such that the "true" damage signal can be reconstructed. The output signal of the summers 110 and 116 is one such reconstructed damage signal for the outer ring damage and the inner ring damage which is thus proportional to the damage length and is faithful to the damage length.

From this reconstructed signal, at this point by means of two so-called period form filters 124 disruptive signal portions which have eliminated the periods of the rotation of the supported shaft are eliminated. Filtering of signals with reference to periodic signal portions is described in detail in a parallel patent application. A period form filter is accordingly a device with one signal input which feeds a rotating ring storage which is formed by the cyclically arranged storage elements which are connected according to the rotation frequency in succession to the input, and a synchronization means to bring the rotation frequency into agreement with the period duration of the desired signal portions. As soon as the period form filter has "transiently oscillated", i.e. after a certain number of revolutions, the contents of the storage elements form a signal train with the desired period length which contains essentially only signal portions (summed or averaged over several periods) with this period duration. The period form filters 124 are synchronized to the shaft rotation frequency. The output signal of the summer 110 from which the rotation period portions have been removed is supplied on the one hand to another period form filter 126, which is synchronized to the rollover frequency of the outer ring to separate all signal portions which have the periodicity of one rollover period of the outer ring from the signal in order to further evaluate these signal portions. In doing so the output signal of the period form filter 126 on the one hand is supplied directly to a diagnosis unit 128 and on the other to a sorting unit 130 in which the signal is processed by its being sorted with respect to its amplitude in order to eliminate structures from the signal which can be attributed to phase differences during signal acquisition in the period form filter 126. In amplitude sorting, the discrete amplitude values (in digital period form filters the signal is already digitized, otherwise it is digitized beforehand) of the signal train delivered by the period form filter 126 are sorted according to their magnitude, i.e. a signal train of the same length arises which however now begins for example with the largest amplitude and ends with the smallest.

The output signal of the sorting stage 130 is likewise supplied to the diagnosis unit 128 and represents possible outer ring damage. Furthermore, the output signal of the summer 110 from which the rotation period portions have been removed by the period form filter 124 is supplied to a sorting unit 132 where the signal is subjected to amplitude sorting by amplitude magnitude. The output signal of the sorter 132 represents damage which can originate both from the outer ring and also from the rolling elements. By subtracting the output signals of the two sorters 130 and 132 from one another in a subtractor 134, a signal can be obtained which represents rolling element damage. In order to achieve resolution with respect to the individual rolling elements, the output signal of the differentiator 134 is supplied to another period form filter 136 which is synchronized to the rotation frequency of the bearing cage, its output signal finally being supplied likewise to the diagnosis unit 128. The output signal of the summer 116 from which the rotation period portions have been removed is supplied to a period form filter 138 which is synchronized to the inner ring rollover frequency, the inner ring damage signal obtained in this way being supplied on the one hand directly to the diagnosis unit 128 and on the other, for purposes of correction of phase differences, being amplitude-sorted in a sorter 140.

In the diagnosis unit 128 finally the damage depth is determined from the signal amplitude, while the damage length is determined from the signal characteristic. The damage depth and the damage length determined in this way can be acquired as a function of time, then from the determined time behavior it being possible to extrapolate to the bearing failure time, the bearing failure time being considered the instant at which a bearing ring has only areas of the running surface in which a rolling element which plunges to the maximum degree transfers no force to the damaged bearing ring, i.e. 100% of the running surface is 100% effectively damaged.

To improve the signal evaluation at high frequencies, the output signal of the transducer 10 can also be subjected to envelope curve formation before the described signal conditioning.

I claim:

1. A process for analyzing roller bearings having a plurality of roller elements which contact an inner ring and an outer ring of the roller bearings, said process comprising the steps of:
    recording a signal produced by the rolling motion of said roller bearings using a sensor;
    evaluating the amplitude of the signal in order to determine at least one of a presence of damage and damage depth to a respective running surface of said inner ring and said outer ring, said damage resulting in a depression into said running surface,
    wherein said evaluating is performed using a dynamic model of the roller bearing, and
    wherein at least one of several double-sided contact stiffnesses of the rolling elements are taken into account in order to determine a transfer function based on the relation of a force caused by the present damage and a related output signal of the sensor, the sensor signal being taken into account in the evaluation of the signal amplitude.

2. The process as claimed in claim 1, wherein the transfer function is determined as a function of the damage done to said running surface.

3. The process as claimed in claim 2, wherein said transfer function is used to determine damage done on said running surface.

4. The process as claimed in claim 3, wherein at least one of gravitational, unbalance, centrifugal and axial forces acting upon said plurality of rolling elements are considered in said dynamic model at least to the extent they exceed a predetermined threshold.

5. The process as claimed in claim 4, wherein the mass and stiffness of all machine components coupled to said roller bearing are considered in said dynamic model.

6. The process as claimed in claim 5, wherein when damage is done to said running surface such that at least one of said plurality of rolling elements no longer transfers gravitational, unbalance, centrifugal and axial forces acting upon said plurality roller bearings, a damage depth is determined using said dynamic model.

7. The process as claimed in claim 6, wherein the determined damage depth is compared to the damage depth which leads to at least one of said plurality of rolling elements no longer transferring gravitational, unbalance, centrifugal and axial forces.

8. The process as claimed in claim 1, wherein a signal portion with a damage rollover period is separated from the sensor signal, and wherein the separated signal portion is subjected to amplitude evaluation.

9. The process as claimed in claim 8, wherein signal portions having a certain period are eliminated from the sensor signal and remaining signal portions are subjected to amplitude evaluation.

10. Process as claimed in claim 9, wherein a three-dimensional extent of damage depth is determined from the separated signal portion.

11. The process as claimed in claim 10, wherein a damage length is determined by sorting the separated signal portion by its amplitudes.

12. The process as claimed in claim 11, wherein separating the signal portion takes place with at least one period form filter.

13. The process as claimed in claim 12, wherein said at least one period form filter comprises a signal which operates to feed a rotating ring storage formed by a plurality of cyclically arranged storage elements connected according to a rotation frequency in succession to said signal input, and a synchronization means to synchronize the rotation frequency with the duration of the rollover period of the damage.

14. The process as claimed in claim 11, wherein the damage depth and the damage length are determined as a function of time.

15. The process as claimed in claim 14, wherein a failure instant of the roller bearing is extrapolated from a determined time behavior of the damage depth and the damage length.

16. The process as claimed in claim 15, wherein the failure instant is a time at which at least one of said inner ring and said outer ring has only areas of the running surface in which at least one of said plurality of rolling elements plunges to a maximum degree such that it no longer transfers force to its respective inner ring and said outer ring.

17. The process as claimed in claim 1, wherein at least some of the parameters which make up the dynamic model are at least one of verified and corrected by verifying the results delivered by the model and wherein said parameters.

18. The process as claimed in claim 17, wherein said parameters are evaluated with a confidence factor which reflects an origin of a respective parameter.

19. The process as claimed in claim 18, wherein the correction of the parameters is performed by compensation calculation with said parameters being weighted according to their respective confidence factor.

20. The process as claimed in claim 19, wherein any finding of damage using the dynamic model is verified by analyzing said roller bearing, and wherein the confidence factors are changed according to the result of the verification.

21. The process as claimed in claim 20, wherein in the presence of damage, the resonant frequencies of said roller bearing is determined using the sensor signal, and wherein the stiffness of the machine components coupled to said roller bearing are at least one of verified and corrected using said resonant frequencies.

22. The process as claimed in claim 1, wherein the dynamic model is made for treating distributed mass-spring vibration systems.

23. The process as claimed in claim 22, wherein said dynamic model is created using finite element analysis.

24. The process as claimed in claim 22, further including a second sensor mounted on a bearing foundation.

25. The process as claimed in claim 22, wherein at least some of the parameters of the dynamic model are determined using an impact test such that said roller bearing is stationary and a machine component which is coupled to said roller bearing is excited in a pulse-like manner and a system response is acquired using said second sensor.

26. The process as claimed in claim 1, wherein an acceleration signal, a velocity signal and a path signal are determined and added in weighted form with the resultant signal analyzed with respect to damage to at least one of said outer ring and said plurality of rolling elements.

27. The process as claimed in claim 26, wherein the weighted form is determined using the dynamic model.

28. The process as claimed in claim 27, wherein frequency-dependent transfer functions for the velocity signal and the path signal are determined using the dynamic model and the velocity signal and the path signal are weighted such that their respective transfer functions have a value of 1 at a resonant frequency between a shaft to which said roller bearing is mounted and a bearing block of said roller bearing.

29. The process as claimed in claim 28, wherein the acceleration signal is acquired using said sensor and wherein the velocity signal and the path signal are formed using said acceleration signal.

30. The process as claimed in claim 29, wherein a first derivative and a second derivative of the acceleration signal are formed and used in the damage analysis.

31. The process as claimed in claim 30, wherein a weighted sum is formed from the acceleration signal, the first derivative, the second derivative, the velocity signal and the path signal, and the resultant sum signal is analyzed with respect to damage to said inner ring.

32. The process as claimed in claim 1, wherein a resulting load direction of the gravitational, unbalance, centrifugal and axial forces acting upon said roller bearing is determined and considered in the signal evaluation of an angle between a coupling site of the sensor and the resulting load direction.

33. A apparatus for analyzing a roller bearing which has been installed in a machine, said apparatus comprising:

a sensor for acquiring a signal produced by the movement of rolling elements of said roller bearings;

a signal processing device for processing the signal which has been picked up by said sensor;

a signal evaluation device for evaluating an amplitude of the processed signal in order to determine at least one of a presence of damage and a depth of damage to a running surface of said roller bearing, wherein said signal processing device has means for processing a signal using a dynamic model of the roller bearing, said dynamic model taking into account at least one of several double-sided contact stiffnesses of the rolling elements in order to determine a transfer function based on the relation of a force caused by the present damage and a related output signal of the sensor, the sensor signal being taken into account in the evaluation of the signal amplitude.

* * * * *